United States Patent [19]

Richardson et al.

[11] Patent Number: 4,616,027

[45] Date of Patent: Oct. 7, 1986

[54] ANTIFUNGAL 1-ARYL-1-FLUOROALKYL-2-(1H-1,2,4-TRIAZOL-1-YL)ETHANOLS

[75] Inventors: Kenneth Richardson; Peter J. Whittle, both of Canterbury, Great Britain

[73] Assignee: Pfizer Inc., New York, N.Y.

[21] Appl. No.: 517,183

[22] Filed: Jul. 25, 1983

[30] Foreign Application Priority Data

Aug. 14, 1982 [GB] United Kingdom ................ 8223459
Nov. 2, 1982 [GB] United Kingdom ................ 8231309

[51] Int. Cl.$^4$ ................ A01N 43/653; C07D 249/08
[52] U.S. Cl. ................ 514/383; 260/665 R; 260/665 G; 546/210; 548/262; 549/563; 568/335; 568/419; 568/812
[58] Field of Search ................ 548/262; 546/210; 424/269, 263; 514/383

[56] References Cited

U.S. PATENT DOCUMENTS 4,243,405  1/1982  Balasubramanyan et al. ...... 424/245
4,386,088  5/1983  Kranz et al. ........................ 424/269

FOREIGN PATENT DOCUMENTS 15756    9/1980  European Pat. Off. ............ 548/262
0031911  7/1981  European Pat. Off. ............ 424/269
47594    3/1982  European Pat. Off. ............ 548/262
48548    3/1982  European Pat. Off. ............ 424/269

OTHER PUBLICATIONS

Burger, Medicinal Chemistry (Second Edition, New York, 1960), p. 1055.

Primary Examiner—Alton D. Rollins
Attorney, Agent, or Firm—Charles J. Knuth; Albert E. Frost; Paul D. Thomas

[57] ABSTRACT

Compounds of the general formula

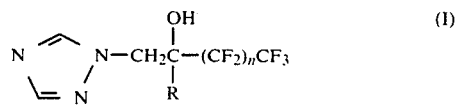

or a pharmaceutically or agriculturally acceptable acid addition salt thereof wherein R is 5-chloro-2-pyridyl, phenyl or phenyl substituted by from one to three substituents, each independently selected from F, Cl, Br, I, $CF_3$, ($C_1$-$C_4$)alkyl and ($C_1$-$C_4$)alkoxy; and n is zero or an integer from 1 to 5; method for their use in combatting fungal infections in plants, seeds and animals, including humans; and pharmaceutical and agricultural compositions containing them.

15 Claims, No Drawings

ANTIFUNGAL 1-ARYL-1-FLUOROALKYL-2-(1H-1,2,4-TRIAZOL-1-YL)ETHANOLS

BACKGROUND OF THE INVENTION

This invention relates to novel triazole derivatives having antifungal activity which are useful in the treatment of fungal infections in animals, including humans, and as agricultural fungicides.

Published European Patent Application Nos. 15,756; 47,594 and 48,548 disclose triazole compounds of the formula $$\begin{array}{c} \text{OH} \\ | \\ N \diagdown \diagup N-CH_2C-R^1 \\ \diagdown N \diagup \quad | \\ \quad\quad R^2 \end{array} \quad (VI)$$

wherein $R^1$ is alkyl, cycloalkyl or optionally substituted phenyl and $R^2$ is phenyl or benzyl, each of which is optionally substituted, e.g., with halogen; methods for their use as plant fungicides and plant growth regulators; and pharmaceutical and veterinary compositions containing them.

Published European Patent Application No. 69,442 discloses difluorophenyl-1,3-bis-triazolylpropan-2-ol having antifungal activity.

SUMMARY OF THE INVENTION

According to the invention, there are provided compounds of the formula $$\begin{array}{c} \text{OH} \\ | \\ N \diagdown \diagup N-CH_2-C-(CF_2)_n-CF_3 \\ \diagdown N \diagup \quad | \\ \quad\quad R \end{array} \quad (I)$$

their O-esters and O-ethers, where R is a phenyl group optionally substituted by 1 to 3 substituents each independently selected from F, Cl, Br, I, trifluoromethyl, $(C_1-C_4)$alkyl and $(C_1-C_4)$alkoxy, or R is a 5-chloropyrid-2-yl group; and n is zero or an integer of from 1 to 5; or their pharmaceutically or agriculturally acceptable acid addition salts.

The invention also provides a pharmaceutical composition comprising an antifungal amount of a compound of the formula (I) or an O-ester, O-ether or pharmaceutically acceptable acid addition salt thereof, together with a pharmaceutically acceptable diluent or carrier.

The invention further provides a compound of the formula (I) or an O-ester, O-ether or pharmaceutically acceptable acid addition salt thereof, for use in medicine, in particular for treating fungal infections in animals, including humans.

The invention further includes an agricultural composition suitable for use on a plant or seed comprising an antifungal amount of a compound of the formula (I), or an O-ester, O-ether or agriculturally acceptable acid addition salt thereof, together with an agriculturally acceptable diluent or carrier.

It also provides a method of treating an animal, including a human being, having a fungal infection, which comprises administering to the animal an antifungal effective amount of a compound of the formula (I), or an O-ester, O-ether or pharmaceutically acceptable acid addition salt thereof.

The invention also includes a method of treating a seed or plant having a fungal infection, which comprises administering to the plant or seed, or to the locus of said plant, an antifungally effective amount of a compound of the formula (I) or of an agriculturally acceptable acid addition salt thereof.

When R is said optionally substituted phenyl group, it is preferably trifluoromethylphenyl or phenyl substituted by 1 to 3 substituents, more preferably 1 or 2 substituents, each independently selected from F, Cl, Br and I. Particularly preferred values of R include 4-fluorophenyl, 4-chlorophenyl, 4-trifluoromethylphenyl, 2-fluorophenyl, 2,4-dichlorophenyl, 2,4-difluorophenyl, 2-fluoro-4-chlorophenyl, 2,5-difluorophenyl, 2,4,6-trifluorophenyl and 4-bromo-2,5-difluorophenyl.

R is most preferably 2,4-dichlorophenyl or 2,4-difluorophenyl.

"n" is preferably 0, 1 or 2, and is most preferably 0 or 1.

The O-ethers of the compounds of the formula (I) include, for example, the $(C_1-C_6)$alkyl, $(C_2-C_4$ alkenyl)methyl, $(C_2-C_4$ alkynyl)methyl, aryl (e.g., phenyl) and aralkyl [e.g., benzyl optionally ring substituted by halo, $(C_1-C_4)$alkyl or $(C_1-C_4)$alkoxy] esters.

The O-esters of the compounds of the formula (I) include, for example, the $(C_2-C_4)$alkanoyl and aroyl [e.g., benzoyl, optionally substituted by halo, $(C_1-C_4)$alkyl or $(C_1-C_4)$alkoxy] esters.

The preferred O-ester is the acetate.

Especially preferred invention compounds include:

2-(2,4-difluorophenyl)-1-(1H-1,2,4-triazol-1-yl)-3,3,3-trifluoropropan-2-ol, 2-(2,4-dichlorophenyl)-1-(1H-1,2,4-triazol-1-yl)-3,3,3-trifluoropropan-2-ol, 2-(2,4-difluorophenyl)-3,3,4,4,4-pentafluoro-1-(1H-1,2,4-triazol-1-yl)butan-2-ol, 2-(2,4-difluorophenyl)-3,3,4,4,5,5,5-heptafluoro-1-(1H-1,2,4-triazol-1-yl)pentan-2-ol, 2-(4-bromo-2,5-difluorophenyl)-1-(1H-1,2,4-triazol-1-yl)-3,3,3-trifluoropropan-2-ol, and 2-(4-trifluoromethylphenyl)-3,3,4,4,4-pentafluoro-1-(1H-1,2,4-triazol-1-yl)butan-2-ol.

DETAILED DESCRIPTION OF THE INVENTION

The compounds of the formula (I) in which n is zero are prepared, for example, by reacting an oxirane of the formula $$\begin{array}{c} \quad\quad O \\ \quad\quad \diagup \diagdown \\ CF_3-C-\!\!-\!\!-\!\!-CH_2 \\ \quad | \\ \quad R \end{array} \quad (II)$$

where R is as defined for formula (I), with 1,2,4-triazole, preferably in the presence of a base, e.g., $K_2CO_3$. Alternatively an alkali metal salt of 1,2,4-triazole is used, preparable, e.g., from the triazole and NaH. Typically the reaction is carried out by heating the reactants together at a temperature of from about 50° up to 130° C. in a suitable organic solvent, e.g., dimethyl formamide, for up to about 24 hours. The product is isolated and purified by conventional methods. For example, the product is isolated by partition between water and a water immiscible solvent, e.g., ethyl acetate and the solvent evaporated to yield a crude product which is purified by chromatography or by recrystallization from a suitable solvent or solvent mixture.

The oxiranes (II) are obtainable conventionally, generally from the ketones of the formula

This is achieved, for example, by the reaction of (III) with dimethyloxosulphonium methylide prepared from trimethylsulphoxoium iodide and either (a) sodium hydride in dimethylsulphoxide, or (b) cetrimide (cetyltrimethylammonium bromide) and sodium hydroxide in a mixture of water and toluene or water and 1,1,1-trichloroethane. The reaction using sodium hydride is typically carried out by stirring sodium hydride with trimethylsulphoxonium iodide at, e.g., room temperature. Dimethylsulphoxide (DMSO) is then added dropwise and the mixture stirred for about 30 minutes, after which time the ketone (III), dissolved in DMSO, is added. The desired product is ordinarily obtained by stirring at room temperature for about an hour. The reaction using cetrimide is typically carried out by stirring the ketone (III), trimethylsulphoxonium iodide and cetrimide in a mixture of 1,1,1-trichloroethane and aqueous sodium hydroxide solution for about two hours at, e.g., 70°–100° C. While in either case the oxirane product (II) can be isolated, if desired, it is often more convenient to convert this in situ to the desired product.

The ketones (III) are either known compounds or can be prepared conventionally, e.g.:

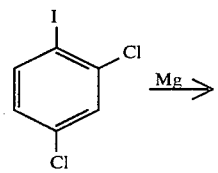

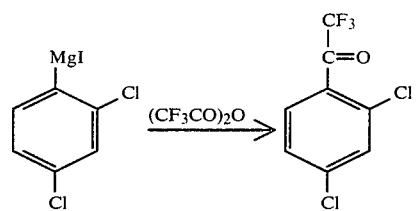

Alternatively, the compounds of the formula (I) in which n is zero are prepared as follows:

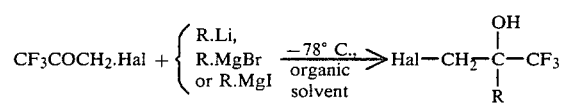

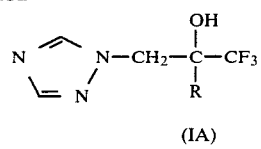

An alkali metal salt of 1,2,4-triazole (preparable e.g., from NaH and the triazole) can be used in place of 1,2,4-triazole/K$_2$CO$_3$.

In a typical procedure, the halo-ketone (IV) and the lithio or Grignard reagent are stirred together in e.g., diethylether at −78° C. for about one hour. The intermediate halo-alkanol can then be recovered conventionally, if desired. The halo-alkanol (V) and 1,2,4-triazole are then heated in e.g., dimethylformamide at 50°–130° C., in the presence of a base such as potassium carbonate for up to about 24 hours. The product (IA) is recovered in a conventional manner, e.g., as described below.

The compounds of the formula (I) in which n is an integer of from 1 to 5 can be prepared analogously to the method described above for the preparation of the compounds (IA), i.e.,

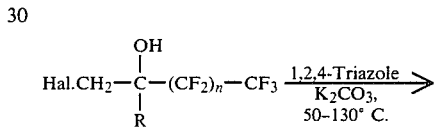

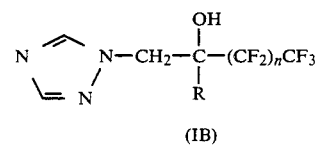

[Hal = Cl or Br and n is 1 to 5].

The reaction is carried out under similar conditions to those previously described, e.g., by heating in dimethylformamide at up to 130° C. for about 24 hours. The product is recovered in a conventional manner, e.g., as described above for compounds of formula (I) wherein n is zero. Again, the starting materials are preparable conventionally, e.g.,

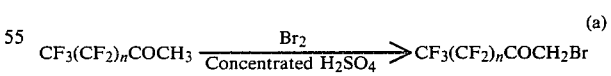

[see e.g., J. Amer. Chem. Soc., 78, 2268–70 (1956)]

or

-continued

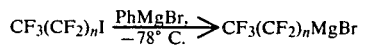

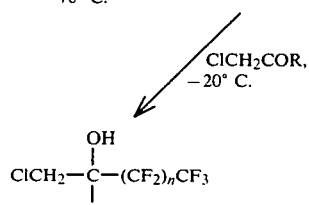

$$ClCH_2-\underset{R}{\underset{|}{\overset{OH}{\overset{|}{C}}}}-(CF_2)_nCF_3$$

n = 1 to 5.

The O-ethers can be made conventionally, e.g., by treating an alkali metal salt of a compound of the formula (I), e.g., a lithium or sodium salt, with the appropriate halide, e.g., an alkyl, alkenylmethyl, alkynylmethyl or aralkyl halide. O-Esters can be made by treating an alkali metal salt of compound (I) with the appropriate acid chloride, bromide or anhydride.

All the compounds of the invention contain an optically active center and the invention includes both the resolved and unresolved forms.

Pharmaceutically and agriculturally acceptable acid addition salts of the compounds of the formula (I) are those formed from strong acids which form non-toxic acid addition salts, such as hydrochloric, hydrobromic, sulphuric, oxalic and methanesulphonic acids.

The salts are obtained by conventional procedures, e.g., by mixing solutions containing equimolar amounts of the free base and desired acid, and the required salt is collected by filtration, if insoluble, or by evaporation of the solvent.

Also included are the alkali metal salts, preparable conventionally.

The compounds of the formula (I) and their O-esters, O-ethers and pharmaceutically acceptable salts are antifungal agents, useful in combatting fungal infections in animals, including humans. For example, they are useful in treating topical fungal infections in man caused by, among other organisms, species of Candida, Trichophyton, Microsporum or Epidermophyton, or in mucosal infections caused by *Candida albicans* (e.g., thrush and vaginal candidiasis). They can also be used in the treatment of systemic fungal infections caused by, for example, *Candida albicans, Cryptococcus neoformans, Aspergillus fumigatus,* Coccidioides, Paracoccidioides, Histoplasma or Blastomyces.

The in vitro evaluation of the antifungal activity of the compounds can be performed by determining the minimum inhibitory concentration (m.i.c.) which is the concentration of the test compounds in a suitable medium at which growth of the particular microorganism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other microorganisms used in such tests can include *Cryptococcus neoformans, Aspergillus fumigatus,* Trichophyton spp; Microsporum spp; *Epidermophyton floccosum, Coccidioides immitis* and *Torulopsis glabrata*.

The in vivo evaluation of the compounds can be carried out at a series of dose levels by intraperitoneal or intravenous injection or by oral administration, to mice which are inoculated with a strain of *Candida albicans*. Activity is based on the survival of a treated group of mice after the death of an untreated group of mice following 48 hours observation. The dose level at which the compound provides 50% protection against the lethal effect of the infection, the $PD_{50}$ in mg/kg, is noted. The in vivo oral $PD_{50}$ values for selected compounds of formula (I) by oral administration to mice inoculated with a lethal dose of *Candida albicans*, as described above, are summarized in the table.

| Compound of Example No. | Oral $PD_{50}$ (mg/kg.) |
| --- | --- |
| 1 | 0.3 |
| 2 | 0.1 |
| 4 | 0.1 |
| 5 | 0.1 |
| 6 | 1.5 |
| 7 | 1.5 |
| 8 | 0.1 |
| 9 | 0.15 |
| 10 | 0.2 |
| 11 | 0.2 |
| 12 | 0.1 |
| 13 | 0.2 |
| 14 | 0.4 |
| 15 | 0.1 |
| 16 | 0.2 |

The most preferred compounds based on their economy and antifungal activity are the products of Examples 2, 4 and 9.

For human use, the antifungal compounds of the formula (I) (or a salt, ester or ether thereof) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response to the particular patient. The above dosages are exemplary of the average case; there can, of course, be individual instances where higher or lower dosage ranges are merited, and such are within the scope of this invention.

Alternatively, the antifungal compounds of the formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their O-ethers, O-esters and salts also have activity against a variety of plant pathogenic fungi, including for example, various rusts, mildews and moulds, and the compounds are, therefore, useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Microorganisms used in such tests include *Cochliobolus carbonum, Pyricularia oryzae, Glomerella cingulata, Penicillium digitatum, Botrytis cinerea* and *Rhizoctonia solani.*

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example, they can be applied directly to the plant foliage, stems, branches, seeds or roots or to the soil or other growing medium, and they may be used not only to eradicate disease, but also prophylactically to protect the plants or seeds from attack.

The following Examples illustrate the invention. All temperatures are in °C. Ratios of solvent mixtures are by volume. Percentages are by weight unless otherwise noted.

EXAMPLE 1

2-(4-Chlorophenyl)-1-(1H-1,2,4-triazol-1-yl)-3,3,3-trifluoropropan-2-ol

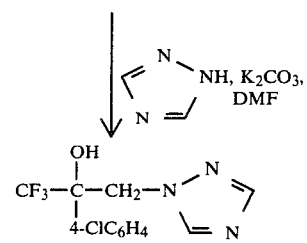

(known)

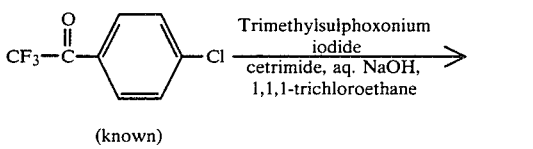

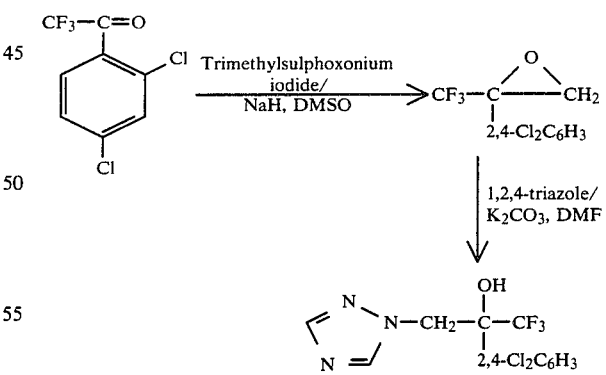

2,2,2-Trifluoro-4'-chloroacetophenone (0.8 g, 3.84 mmole), trimethylsulphoxonium iodide (1.02 g, 4.6 mmole) and cetyltrimethylammonium bromide (0.1 g, 0.27 mmole) were stirred in a mixture of 1,1,1-trichloroethane (40 ml) and 18% sodium hydroxide solution (20 ml) at 75° C. for two hours. The mixture was then allowed to cool, the organic layer was separated, evaporated, and the residue was stirred in dimethylformamide (50 ml) with 1,2,4-triazole (1 g, 14.5 mmole) and anhydrous potassium carbonate (2 g, 14.5 mmole) at 90° for four hours. The mixture was then allowed to cool, ethyl acetate (100 ml) and water (50 ml) were added and the aqueous layer was separated. The organic layer was then washed six times with water (200 ml in total), dried over magnesium sulphate, and evaporated to give a gum (104 mg) which was chromatographed on silica (230-400 mesh), eluting with ethyl acetate, to give as a colorless solid the title compound, 84 mg, (8%). One recrystallization from dichloromethane/hexane gave colorless crystals, 64 mg, m.p. 117°-118° C.

Analysis %:

Required for $C_{11}H_9ClF_3N_3O$: C, 45.28; H, 3.09; N, 14.4.

Found: C, 45.36; H, 3.06; N, 14.76.

EXAMPLE 2

2-(2,4-Dichlorophenyl)-1-(1H-1,2,4-triazol-1-yl)-3,3,3-trifluoropropan-2-ol

Sodium hydride as a 60% oil dispersion (0.36 g, 9.05 mmole) was washed with distilled hexane, dried, and stirred at room temperature with trimethylsulphoxonium iodide (1.99 g, 9.05 mmole). Dimethylsulphoxide (10 ml) was then added dropwise over five minutes and the mixture was stirred until effervescence had ceased (about 30 minutes). A solution of 2',4'-dichloro-2,2,2-trifluoroacetophenone (2 g, 8.23 mmole) in dimethylsulphoxide (8 ml) was then added and the mixture was stirred at room temperature for 45 minutes. Water (50 ml) and ether (100 ml) were then added and the organic layer was separated, washed once with water, dried over magnesium sulphate and evaporated to give a pale yellow liquid (1.8 g) which was added to a mixture of 1,2,4-triazole (2 g, 29 mmole) and anhydrous potassium carbonate (4 g, 29 mmole) in dimethylformamide (100 ml). This mixture was heated at about 75° C. for 18 hours and then poured into a mixture of ethyl acetate (500 ml) and water (200 ml). The organic layer was separated, washed with water (5×100 ml), dried over magnesium sulphate, and evaporated to give a pale yellow tacky solid which was chromatographed on silica (230-400 mesh) eluting with ethyl acetate, to give, after recrystallization from ethyl acetate, the title compound, 1.49 g (56%), m.p. 133.5-134.5° C.

Analysis %:

Required for $C_{11}H_8Cl_2F_3N_3O$: C, 40.49; H, 2.45; N, 12.88.

Found: C, 40.58; H, 2.58; N, 12.96.

EXAMPLE 3

The following illustrate pharmaceutical compositions for the treatment of fungal infections:

(a) Capsule: 71 parts by weight of the compound of Example 1 are granulated with 3 parts maize starch and 22 parts lactose and then a further 3 parts maize starch and 1 part magnesium stearate are added. The mixture is regranulated and filled into hard gelatin capsules.

(b) Cream: 2 parts by weight of the compound of Example 1 are dissolved in 10 parts of propylene glycol and mixed into 88 parts of a vanishing cream base.

(c) Pessary: 2 parts by weight of the compound of Example 2 are suspended in 98 parts of a warm liquified suppository base which is poured into moulds and allowed to solidify.

EXAMPLE 4

2-(2,4-Difluorophenyl)-1-(1H-1,2,4-triazol-1-yl)-3,3,3-trifluoropropan-2-ol

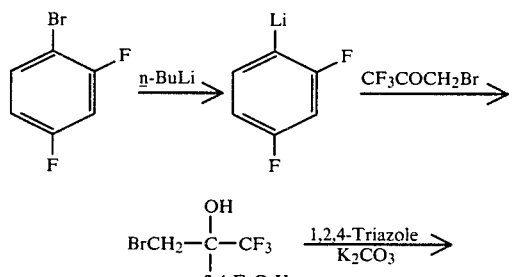

A hexane solution of n-butyllithium (1.55 M, 9.6 ml, 14.9 mmole) was added to diethylether (6 ml) and the solution was cooled to −78° C. A solution of 2,4-difluorobromobenzene (3.03 g, 15.7 mmole) in diethylether (100 ml) was added dropwise over 15 minutes. A solution of 1-bromo-3,3,3-trifluoropropan-2-one (2.4 g, 12.6 mmole) in diethylether (100 ml) was then added dropwise over 15 minutes and the mixture was stirred at −78° C. for a further 30 minutes. A solution of glacial acetic acid (2 ml) in diethylether (5 ml) was then added, followed by water (15 ml) and the mixture was allowed to warm to 0° C. The aqueous layer was separated and washed with diethylether (2×30 ml). The combined diethylether extracts were dried over magnesium sulphate, evaporated, and the residual oil was dissolved in dimethylformamide (40 ml). 1,2,4-Triazole (2.5 g, 36.2 mmole) and anhydrous potassium carbonate (10 g, 72.5 mmole) were then added to this solution and the mixture was stirred and heated at 70° C. for 18 hours. The mixture was then cooled, poured into water (150 ml) and extracted with ethyl acetate (3×100 ml). The combined ethyl acetate extracts were washed with water (100 ml), dried over magnesium sulphate, and evaporated. The residue was chromatographed on silica (230-400 mesh), eluting with ethyl acetate:hexane, 60:40 by volume, to give, after one recrystallization from ethyl acetate/hexane, the title compound, 1.7 g (47%), m.p. 110°-111° C.

Analysis %:

Required for $C_{11}H_8F_5N_3O$: C, 45.05; H, 2.75; N, 14.33.

Found: C, 45.16; H, 2.73; N, 14.56.

EXAMPLES 5-8

The compounds in Examples 5-8 were prepared similarly to the method described in the previous Example, using the appropriate aryllithium (Examples 5, and 6,) or Grignard reagent (Examples 7 and 8). In Example 7, tetrahydrofuran was used instead of dimethylformamide in the final stage of the reaction.

$$N{\overset{\diagup}{\underset{\diagdown}{\rceil}}}N\!-\!CH_2\!-\!\overset{OH}{\underset{R}{C}}\!-\!CF_3$$

| Example No. | R | % Yield | m.p. (°C.) | Analysis % (Theoretical in brackets) | | |
|---|---|---|---|---|---|---|
| | | | | C | H | N |
| 5 | 3,4-F,Br-phenyl | 67 | 148-50 | 35.90 (35.51 | 1.93 1.90 | 11.42 11.29) |
| 6 | 4-CF₃-phenyl | 21 | 94-96 | 44.36 (44.32 | 2.76 2.79 | 13.13 12.92) |
| 7 | 4-F-phenyl | 23 | 134-6 | 47.78 (48.00 | 3.20 3.30 | 15.49 15.27) |
| 8 | 3-F,4-Cl-phenyl | 0.4 | 95° | 43.4 (42.7 | 2.7 2.6 | 13.0 13.6) |

EXAMPLE 9

(A) 1-Bromo-3,3,4,4,4-pentafluorobutanone

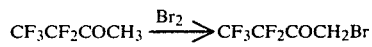

$$CF_3CF_2COCH_3 \xrightarrow{Br_2} CF_3CF_2COCH_2Br$$

Methyl pentafluoroethyl ketone (3.9 g, 0.02407 mole) (JACS, 78, 2268-70 [1956]) was stirred in concentrated sulphuric acid (10 ml) at room temperature under a dry-ice condenser. Bromine (1.92 g; 0.012035 mole) was added slowly over two hours with vigorous stirring. The mixture was then stirred for one hour at room temperature and then at 50° C. for one hour. The resulting amber solution was distilled at atmospheric pressure, yielding one main fraction of 4.41 g (76%), boiling at 94–97° C. The mass spectrum confirmed the structure, showing parent ions at 240 and 242 m/e corresponding to $C_4H_2BrF_5O$ (2 isotopes of Br).

(B) 2-(2,4-Difluorophenyl)-3,3,4,4,4-pentafluoro-1-(1H-1,2,4-triazol-1-yl)-butan-2-ol

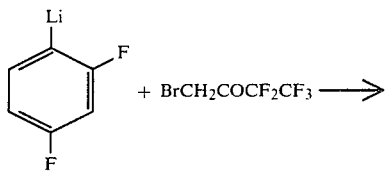

n-Butyl lithium (3.32 ml of a 1.5 molar solution in hexane; 0.00498 mole) in diethylether (5 ml) was cooled and stirred at −78° C. A solution of 2,4-difluorobromobenzene (1.0 g; 0.00519 mole) in ether (8 ml) was added slowly over 15 minutes. The reaction mixture was held for 15 minutes at −78° C. 1-Bromo-3,3,4,4,4-pentafluorobutanone (1.0 g; 0.00415 mole) in 6 ml of ether was then added over 15 minutes at −78° C. The mixture was stirred for 30 minutes at −78° C. Acetic acid (0.7 g) in ether (5 ml) was added followed by water (8 ml), and the mixture was allowed to warm to room temperature. The ether layer was separated and the aqueous layer was washed with 2×15 ml of ether. The combined ether layers were dried over magnesium sulphate and evaporated to give an oil. To this oil were added 1,2,4-triazole (0.86 g; 0.01245 mole); anhydrous potassium carbonate (5.73 g; 0.0415 mole) and anhydrous dimethylformamide (15 ml). The mixture was heated and stirred at 80° C. for 3.5 hours, cooled to room temperature and poured into 150 ml of water. The mixture was then extracted with 3×60 ml methylene chloride, and the combined organic extracts were dried over magnesium sulphate, evaporated and then co-distilled with xylene. The residual brown oil was chromatographed on silica (230–400 mesh) under pressure. Elution with a mixture of ethyl acetate/hexane (60/40 by volume) gave the title compound as a white solid (400 mgs; 28%), melting point 95°–6° C. after crystallization from cyclohexane.

Analysis %:
Required for $C_{12}H_8F_7N_3O$: C, 41.99; H, 2.34; N, 12.24.
Found: C, 41.84; H, 2.28; N, 12.05.

EXAMPLES 10–14

The following compounds were prepared similarly to the previous Example from appropriate starting materials.

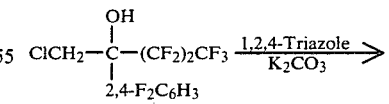

| Example No. | R | % Yield | m.p. (°C.) | Analysis % (Theoretical in brackets) | | |
|---|---|---|---|---|---|---|
| | | | | C | H | N |
| 10 | 2,4-dichlorophenyl | 7 | 109–10 | 38.39 (38.32 | 2.12 2.14 | 11.12 11.17) |
| 11 | 2,5-difluoro-4-bromophenyl | 19.4 | 168–70 | 34.32 (34.14 | 1.67 1.67 | 9.58 9.95) |
| 12 | 4-trifluoromethylphenyl | 14 | 108–10 | 41.98 (41.61 | 2.42 2.42 | 11.16 11.20) |
| 13 | 2-fluorophenyl | 13 | 95–97 | 44.3 (44.3 | 2.7 2.8 | 12.7 12.9) |
| 14 | 4-fluorophenyl | 5.9 | 95–97 | 44.6 (44.3 | 2.8 2.8 | 13.3 12.9) |

EXAMPLE 15

2-(2,4-Difluorophenyl)-3,3,4,4,5,5,5-heptafluoro-1-(1H-1,2,4-triazol-1-yl)-pentan-2-ol

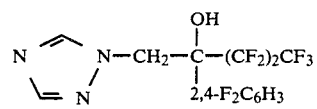

To a solution of heptafluoropropyl iodide (5 g, 0.017 mole) in ether (20 ml) cooled to −78° C. was added phenylmagnesium bromide (5.6 ml of a 3 molar solution in ether, 0.017 mole) dropwise at such a rate that the temperature of the reaction mixture did not exceed −50° C. When all the phenylmagnesium bromide had been added, the mixture was stirred at −50° C. for 0.5 hours and then cooled again to −78° C. A solution of 2-chloro-2',4'-difluoroacetophenone (3.6 g, 0.019 mole) in ether (20 ml) was added dropwise at such a rate that the temperature of the reaction mixture did not exceed −50° C. and, when the addition was complete, the reaction mixture was allowed to warm to −20° C. and was stirred at this temperature for two hours. A solution of glacial acetic acid (3 ml) in ether (5 ml) was then added, followed by water (15 ml) and the mixture was allowed to warm to about 5° C. The aqueous phrase was separated and extracted with ether (2×50 ml) and the combined ether extracts were dried (MgSO₄) and evaporated to give a pale yellow oil (6.7 g). This oil was added to a mixture of 1,2,4-triazole (5.87 g, 0.085 mole) and anhydrous potassium carbonate (17.5 g, 0.127 mole) in dimethylformamide (60 ml) and this mixture was stirred at a temperature of 80° C. for three hours. The reaction mixture was then cooled, the dimethylformamide was evaporated and the residue was partitioned between water (200 ml) and ethyl acetate (150 ml). The aqueous layer was separated and extracted with ethyl acetate (3×150 ml). The combined ethyl acetate extracts were washed successively with aqueous sodium bisulphite and water, dried (MgSO₄), evaporated and the residue was flash chromatographed on silica (230-400 mesh), eluting with a mixture of hexane: isopropyl alcohol:0.88 ammonium hydroxide, 80:20:1.5 by volume, to yield, after one recrystallization from hexane:dichloromethane, the title compound, 1.51 g (23%), m.p. 128° C.

Analysis %:
Required for $C_{13}H_8F_9N_3O$: C, 39.7; H, 2.1; N, 10.7.
Found: C, 39.8; H, 2.0; N, 10.6.

EXAMPLE 16

2-(4-Fluorophenyl)-3,3,4,4,5,5,5-heptafluoro-1-(1H-1,2,4-triazol-1-yl)-pentan-2-ol was prepared similarly to the previous Example from appropriate starting materials, yield 7%, m.p. 126°–127° C.

Analysis %
Required for $C_{13}H_9F_8N_3O$: C, 41.6; H, 2.4; N, 11.2
Found: C, 41.9; H, 2.4; N, 11.3.

The following Preparation, in which all temperatures are in °C., illustrates the preparation of a novel starting material.

PREPARATION A

2',4'-Dichloro-2,2,2-trifluoroacetophenone

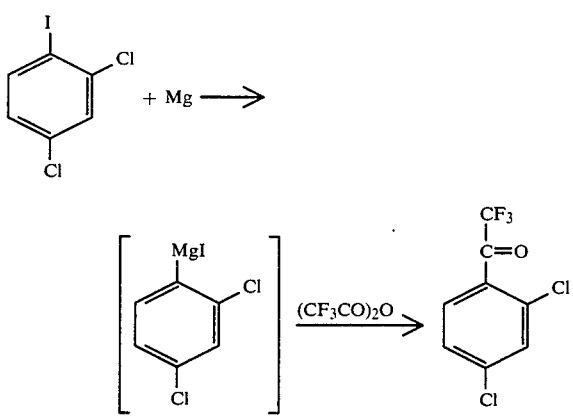

A solution of 2,4-dichlorophenylmagnesium iodide, prepared from 2,4-dichloroiodobenzene (27.3 g, 0.1 mole) and magnesium (3.3 g, 0.138 mole), in ether (150 ml) was added dropwise to a solution of trifluoroacetic anhydride (24 g, 0.114 mole) in ether (20 ml) at −78° C. Stirring was continued at −78° C. for 10 minutes and the mixture was then allowed to warm to room temperature over 4 hours, stirred for a further 18 hours at this temperature and then heated under reflux for 3 hours. The mixture was then cooled and treated with concentrated hydrochloric acid (25 ml) in iced water (125 ml). The ether layer was separated and the aqueous layer was washed a further four times with ether (200 ml in total). The combined ether extracts were washed successively with aqueous sodium bisulphite, aqueous sodium bicarbonate and water, dried over magnesium sulphate and distilled to give as a pale yellow liquid which solidified on cooling, the title compound, 14.2 g (58%), b.p. 46° C. (0.2 mm Hg), m.p. 38° C. m/e 242.

We claim:
1. A compound of the formula

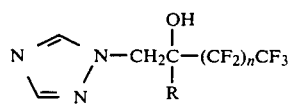

a pharmaceutically or agriculturally acceptable acid addition salt thereof, wherein n is zero, 1 or 2; and R is trifluoromethylphenyl or phenyl substituted by 1 to 3 substituents each independently selected from F, Cl and Br.

2. A compound according to claim 1 wherein R is 4-fluorophenyl, 4-chlorophenyl, 4-trifluoromethylphenyl, 2-fluorophenyl, 2,4-dichlorophenyl, 2,4-difluorophenyl, 2-fluoro-4-chlorophenyl, 2,5-difluorophenyl, 2,4,6-trifluorophenyl or 4-bromo-2,5-difluorophenyl.

3. A compound according to claim 2 wherein R is 2,4-difluorophenyl or 2,4-dichlorophenyl.

4. A compound according to claim 3 wherein R is 2,4-difluorophenyl.

5. A compound according to claim 3 wherein n is zero and R is 2,4-dichlorophenyl.

6. The compound according to claim 2 wherein n is zero and R is 4-bromo-2,5-difluorophenyl.

7. The compound according to claim 2 wherein n is 1 and R is 4-trifluoromethylphenyl.

8. The compound according to claim 4: 2-(2,4-difluorophenyl)-3,3,4,4,5,5,5-heptafluoro-1-(1H-1,2,4-triazol-1-yl)-pentan-2-ol.

9. The compound according to claim 4: 2-(2,4-difluorophenyl)-1-(1H-1,2,4-triazol-1-yl)-3,3,3-trifluoropropan-2-ol.

10. The compound according to claim 4: 2-(2,4-difluorophenyl)-3,3,4,4,4-pentafluoro-1-(1H-1,2,4- triazol-1-yl)butan-2-ol.

11. The compound according to claim 5: 2-(2,4-dichlorophenyl)-1-(1H-1,2,4-triazol-1-yl)-3,3,3-trifluoropropan-2-ol.

12. A pharmaceutical composition comprising an antifungal amount of a compound or pharmaceutically acceptable salt according to claim 1 and a pharmaceutically acceptable diluent or carrier.

13. An agricultural antifungal composition suitable for use on a plant or seed which comprises an antifungal amount of a compound or agriculturally acceptable salt according to claim 1 and an agriculturally acceptable diluent or carrier.

14. A method of treating a fungal infection in an animal in need of such treatment which comprises administration to said animal an antifungal amount of a compound or pharmaceutically acceptable salt according to claim 1.

15. A method of treating a fungal infection in a plant or seed in need of such treatment which comprises administration to said plant or seed an antifungal amount of a compound or agriculturally acceptable salt according to claim 1.

* * * * *